(12) United States Patent
Matsumoto et al.

(10) Patent No.: US 11,647,954 B2
(45) Date of Patent: May 16, 2023

(54) EAR DEVICE FOR HEAT STROKE DETECTION

(71) Applicant: INTERNATIONAL BUSINESS MACHINES CORPORATION, Armonk, NY (US)

(72) Inventors: Keiji Matsumoto, Kanagawa-ken (JP); Bruno Michel, Zurich (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 640 days.

(21) Appl. No.: 16/677,881

(22) Filed: Nov. 8, 2019

(65) Prior Publication Data
US 2021/0137457 A1 May 13, 2021

(51) Int. Cl.
| | | |
|---|---|---|
| *A61B 5/00* | (2006.01) | |
| *A61B 5/01* | (2006.01) | |
| *A61B 5/087* | (2006.01) | |
| *A61B 5/024* | (2006.01) | |

(52) U.S. Cl.
CPC .......... *A61B 5/6817* (2013.01); *A61B 5/0008* (2013.01); *A61B 5/01* (2013.01); *A61B 5/02433* (2013.01); *A61B 5/0878* (2013.01); *A61B 5/4266* (2013.01)

(58) Field of Classification Search
CPC ..... A61B 5/0022; C12N 15/815; G16H 40/20
See application file for complete search history.

(56) References Cited

U.S. PATENT DOCUMENTS

| | | | |
|---|---|---|---|
| 8,961,415 B2 | 2/2015 | LeBoeuf et al. | |
| 10,307,101 B1* | 6/2019 | Miller | A61B 5/7278 |
| 2005/0010273 A1* | 1/2005 | Walker | A61M 25/0662 |
| | | | 607/113 |
| 2007/0110124 A1* | 5/2007 | Shiraki | G01K 1/08 |
| | | | 374/208 |
| 2010/0217099 A1* | 8/2010 | LeBoeuf | A61B 5/021 |
| | | | 600/301 |
| 2015/0131837 A1* | 5/2015 | LeBoeuf | A61B 5/0084 |
| | | | 381/380 |

(Continued)

OTHER PUBLICATIONS

Burrows, "The future is ear: Why "hearables" are finally tech's next big thing", https://www.fastcompany.com/90212065/the-future-is-ear-why-hearables-are-finally-techs-next-big-thing. Aug. 14, 2 019. pp. 1-14.

(Continued)

*Primary Examiner* — Fabricio R Murillo Garcia
(74) *Attorney, Agent, or Firm* — Tutunjian & Bitetto, P.C.; Randy Emillio Tejeda

(57) ABSTRACT

A method is presented for predicting heat stroke of a subject. The method includes an earbud covered with a waterproof moisture permeable membrane allowing for moisture penetration, the earbud including an infrared (IR) temperature sensor for measuring core body temperature of the subject, wherein the IR temperature sensor is covered with a waterproof IR transmittable film to inhibit water drops from contacting a detector of the IR temperature sensor, a first humidity sensor positioned within a sweat flow path within the earbud, a second humidity sensor positioned outside the earbud, and a sodium ion (Na+) concentration sensor for measuring hydration levels of the subject.

19 Claims, 10 Drawing Sheets

(56) References Cited

U.S. PATENT DOCUMENTS

| | | | |
|---|---|---|---|
| 2016/0240061 A1 | 8/2016 | Li et al. | |
| 2017/0127174 A1 | 5/2017 | Burgett et al. | |
| 2017/0258329 A1* | 9/2017 | Marsh | G01J 5/0806 |
| 2019/0117155 A1 | 4/2019 | Cross et al. | |
| 2020/0090636 A1* | 3/2020 | Yang | G10K 11/17854 |
| 2021/0000347 A1* | 1/2021 | Stump | A61B 5/02444 |

OTHER PUBLICATIONS

Daiichi-Kagaku, "Extreme Humidity! Part 21 . . . Type and Selection of Humidity Sensor | Temperature x Humidity x Pressure =", https://www.daiichi-kagaku.co.jp/blog/labo/?p=603&doing_wp_cron=1565795503.3568649291992187500000. Feb. 25, 2016. pp. 1-9.

EverydayHearing, "The Complete Guide to Hearable Technology in 2019", Everyday Hearing, Blog. https://www.everydayhearing.com/hearing-technology/articles/hearables/. May 8, 2019. pp. 1-26.

EvertdayHearing, "Best Hearing Aid Brands of 2019", Everyday Hearing, Blog, https://www.everydayhearing.com/hearing-aids/articles/top-6-most-reputable-hearing-aid-brands/. Aug. 12, 2019. pp. 1-19.

Hikawa, "KDDI launches wearable IoT service to prevent workers from heat stroke" KDDI Launches IoT Service to Prevent Workers' Heatstroke and Other Wearale Wears | IT Leaders. https://it.impressbm.co.jp/articles/-/16120. May 22, 2019. pp. 1-2.

Indiamart, "KSJ Bluetooth Wireless Neckband Headset, Rs 220/piece, E Traders | ID: 12910704791", https://www.indiamart.com./proddetail/bluetooth-wireless-neckband-headset-12910704791.html. Aug. 14, 2019. pp. 1-6.

Nippon, "Water Science Comprehensive Knowledge Information Platform R & D Report", Nippon Foundataion Library (Electronic Library) Water Science Comprehensive Knowledge Information Platform R & D Report. https://nippon.zaidan.info/seikabutsu/2003/00213/contents/0006.htm. Aug. 10, 2019. pp. 1-4.

Shinkachi, "Wearable heat stroke predictor that can measure whole body sweat", Life Care Giken Co., Ltd. Exhibition 2019. http://shinkachi-portal.smj.go.jp/navi/company/smme/19xy6/. Aug. 14, 2019. pp. 1-6.

* cited by examiner

EAR DEVICE FOR HEAT STROKE DETECTION

BACKGROUND

The present invention relates generally to heat stroke detection devices, and more specifically, to a wearable device in an ear of a subject for detecting at least the following bio-markers; core body temperature, sweat rate, and sodium ion concentration.

Heat stroke is a condition that can occur when a person's body gets too hot. Most often, heat stroke occurs when people exercise in very hot and humid weather without drinking enough fluids. But heat stroke can also occur in people who are not exercising. It is especially likely to affect older people and people who have health problems. Also, when people get too hot, they also get "heat cramps" and "heat exhaustion." These conditions are not as serious as heat stroke, but they can lead to heat stroke if they aren't treated.

SUMMARY

In accordance with an embodiment, a wearable device is provided for predicting heat stroke of a subject. The wearable device includes an earbud covered with a waterproof moisture permeable membrane allowing for moisture penetration, the earbud including an infrared (IR) temperature sensor for measuring core body temperature of the subject, wherein the IR temperature sensor is covered with a waterproof IR transmittable film to inhibit water drops from contacting a detector of the IR temperature sensor, a first humidity sensor positioned within a sweat flow path within the earbud, a second humidity sensor positioned outside the earbud, and a sodium ion (Na$^+$) concentration sensor for measuring hydration levels of the subject.

In accordance with another embodiment, a wearable device is provided for predicting heat stroke of a subject. The wearable device includes a pair of earbuds coated with a polymer absorbing membrane, wherein the pair of earbuds include an infrared (IR) temperature sensor for measuring core body temperature of the subject, a pair of humidity sensors for measuring differential humidity between an ear canal of the subject and ambient, and a sodium ion (Na$^+$) concentration sensor for measuring hydration levels of the subject.

In accordance with yet another embodiment, a method for predicting heat stroke of a subject is provided. The method includes covering an earbud with a waterproof moisture permeable membrane that allows for moisture penetration, measuring, by an infrared (IR) temperature sensor, core body temperature of the subject, wherein the IR temperature sensor is covered with a waterproof IR transmittable film to inhibit water drops from contacting a detector of the IR temperature sensor, positioning a first humidity sensor within a sweat flow path within the earbud, placing a second humidity sensor outside the earbud, and measuring, by a sodium ion (Na$^+$) concentration sensor, hydration levels of the subject.

It should be noted that the exemplary embodiments are described with reference to different subject-matters. In particular, some embodiments are described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be described within this document.

These and other features and advantages will become apparent from the following detailed description of illustrative embodiments thereof, which is to be read in connection with the accompanying drawings.

BRIEF DESCRIPTION OF THE DRAWINGS

The invention will provide details in the following description of preferred embodiments with reference to the following figures wherein.

Throughout the drawings, same or similar reference numerals represent the same or similar elements.

DETAILED DESCRIPTION

Figure 1:
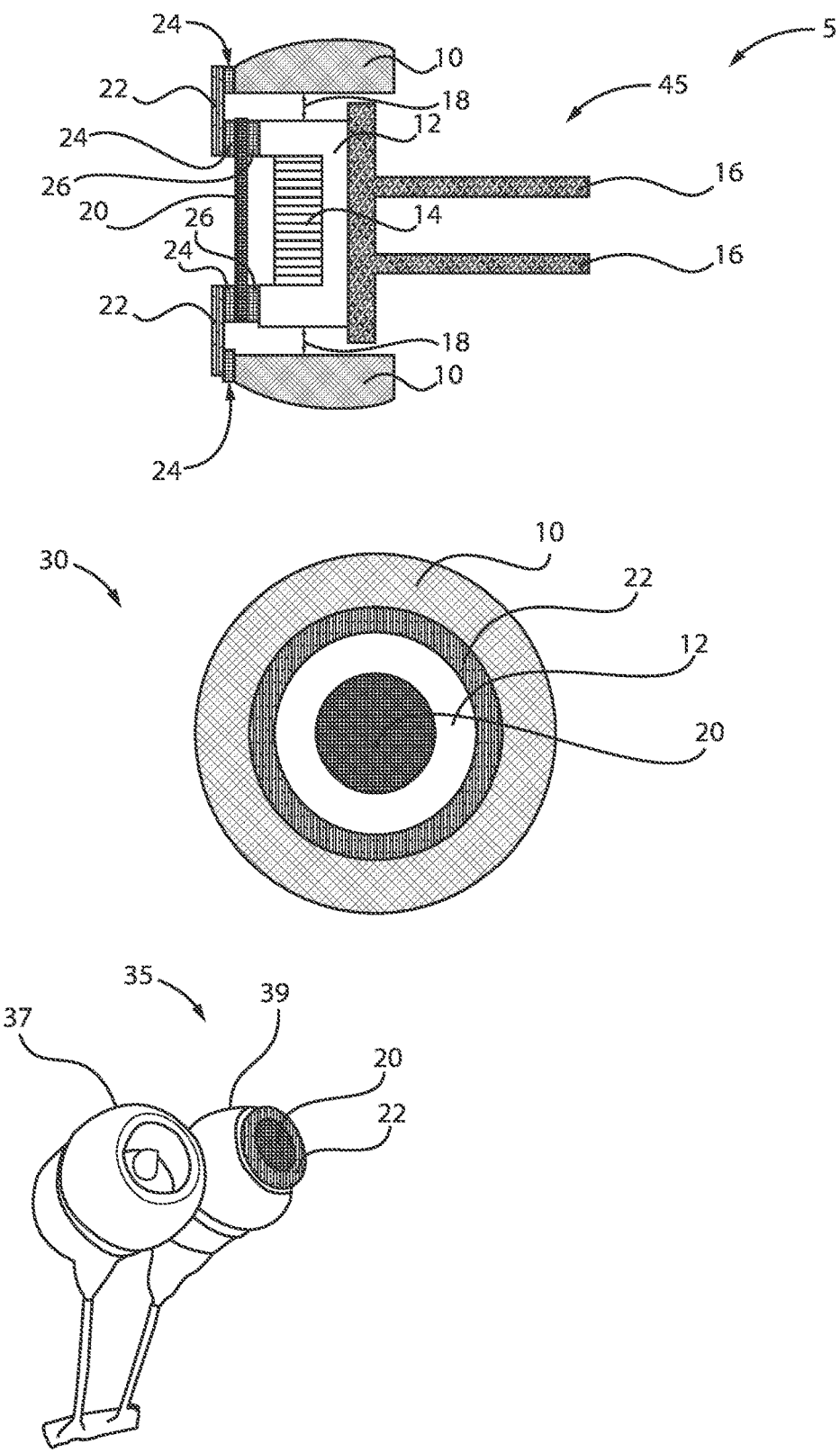
FIG. 1 illustrates several views on an earbud including a waterproof IR transmittable film with hydrophobic surface treatment and a waterproof moisture (humidity) permeable membrane, in accordance with an embodiment of the present invention.

Embodiments in accordance with the present invention provide methods and devices for detecting heat stroke in a subject. There are several bio-markers for early detection of heat stroke. These bio-markers include core body temperature, sweat rate, and sodium ion (Na$^+$) concentration. The core body temperature can be accurately measured from an ear drum of a subject. In accordance thereof, the exemplary embodiments of the present invention present a wearable device for detecting heat stroke. The wearable device can be worn on or in an ear of the subject. The wearable device can detect heat stroke in a subject by measuring at least core body temperature, sweat rate, and sodium ion (Na$^+$) concentration continuously and in real-time.

The wearable device can be attached to an ear of the subject to extract data or information from the ear drum of the subject. An ear drum is considered to reflect the core body temperature in a precise and timely manner, and the temperature of the ear drum is measured by, e.g., a non-contact temperature sensor (e.g., infrared (IR) temperature sensor). However, in the IR temperature measurement, when some water or sweat in an ear exists, the measured result changes and accurate measurements can be difficult.

Embodiments in accordance with the present invention provide methods and devices for covering an IR temperature sensor with an IR transmittable film (waterproof) with hydrophobic surface treatment. This film inhibits a water drop in order to cover the surface of the IR temperature sensor. The IR temperature sensor is located at a front side of an earbud type wearable device. The front side of the IR temperature sensor is almost the same as that of an ear cap. Also the IR temperature sensor does not occupy the whole front side of the ear cap for sweat to come in. Further, the front side of earbud type wearable device is covered with a waterproof moisture (humidity) permeable membrane. This film inhibits a water drop to enter, but moisture can go through, and, thus, doesn't affect the humidity sensor (sweat rate measurement). An opening is made at the upper side of the ear cap for sweat to go to ambient. One humidity sensor is placed on the sweat flow path to ambient and the opening is also covered with a waterproof moisture (humidity) permeable membrane. The other humidity sensor is placed on the sweat flow path in an earbud.

Embodiments in accordance with the present invention provide methods and devices for accurately measuring the temperature of the ear drum even when water or sweat is located in an ear. This can be accomplished by incorporating a sweat sensor in the wearable device. For sweat measurements, a pair of humidity sensors are incorporated or integrated or embedded into the wearable device to measure the differential humidity in the ear canal and the ambient. Additionally, an electrochemical Na$^+$ sensor is also incorporated or integrated or embedded into the wearable device. Other sensors can also be incorporated into the wearable device.

It is to be understood that the present invention will be described in terms of a given illustrative architecture; however, other architectures, structures, substrate materials and process features and steps/blocks can be varied within the scope of the present invention. It should be noted that certain features cannot be shown in all figures for the sake of clarity. This is not intended to be interpreted as a limitation of any particular embodiment, or illustration, or scope of the claims.

FIG. 1 illustrates several views on an earbud including a waterproof IR transmittable film with hydrophobic surface treatment and a waterproof moisture (humidity) permeable membrane, in accordance with an embodiment of the present invention.

Side view 5 illustrates the ear cap 10. An infrared (IR) temperature sensor 45 is placed within the ear cap 10. The outer rim 12 and the detector 14 of the IR temperature sensor 45 are located within the ear cap 10, whereas pins 16 of the IR temperature sensor 45 project beyond the boundary of the ear cap 10. Gaps 18 are formed between the ear cap 10 and the IR temperature sensor 45. Gaps 18 allow for sweat to enter into the ear cap 10. The front side of the IR temperature sensor 45 is almost the same as that of the ear cap 10.

A waterproof IR transmittable film 20 with hydrophobic surface treatment and a waterproof moisture (humidity) permeable membrane 22 are placed in front of the ear bud 10 and the IR temperature sensor 45. The waterproof IR transmittable film 20 is placed directly in front of the IR temperature sensor 45. In particular, the waterproof IR transmittable film 20 is attached to the outer rim 12 of the IR temperature sensor 45 with adhesives 26. The waterproof IR transmittable film 20 extends a diameter of the outer rim 12 of the IR temperature sensor 45. The waterproof moisture (humidity) permeable membrane 22 is attached to the ear bud 10 and the waterproof IR transmittable film 20 by adhesives 24. Adhesives 24, 26 can be constructed by the same or different materials.

Front view 30 illustrates the waterproof IR transmittable film 20 within the outer rim 12 of the IR temperature sensor 45. The waterproof moisture (humidity) permeable membrane 22 is positioned around or surrounding the outer rim 12 of the IR temperature sensor 45. The earbud 10 encompasses all the other layers.

Perspective view 35 illustrates a first earbud 37 and a second earbud 39. The first earbud 37 can be employed for audio capabilities, and can include, e.g., a microphone, a voice pick-up (VPU) sensor, and a speaker. The second earbud 39 can incorporate sensors, such as, e.g., temperature sensors, sweat sensors, Na$^+$ concentration sensors, etc. The second earbud 39 can include the waterproof IR transmittable film 20 and the waterproof moisture (humidity) permeable membrane 22.

Figure 2:
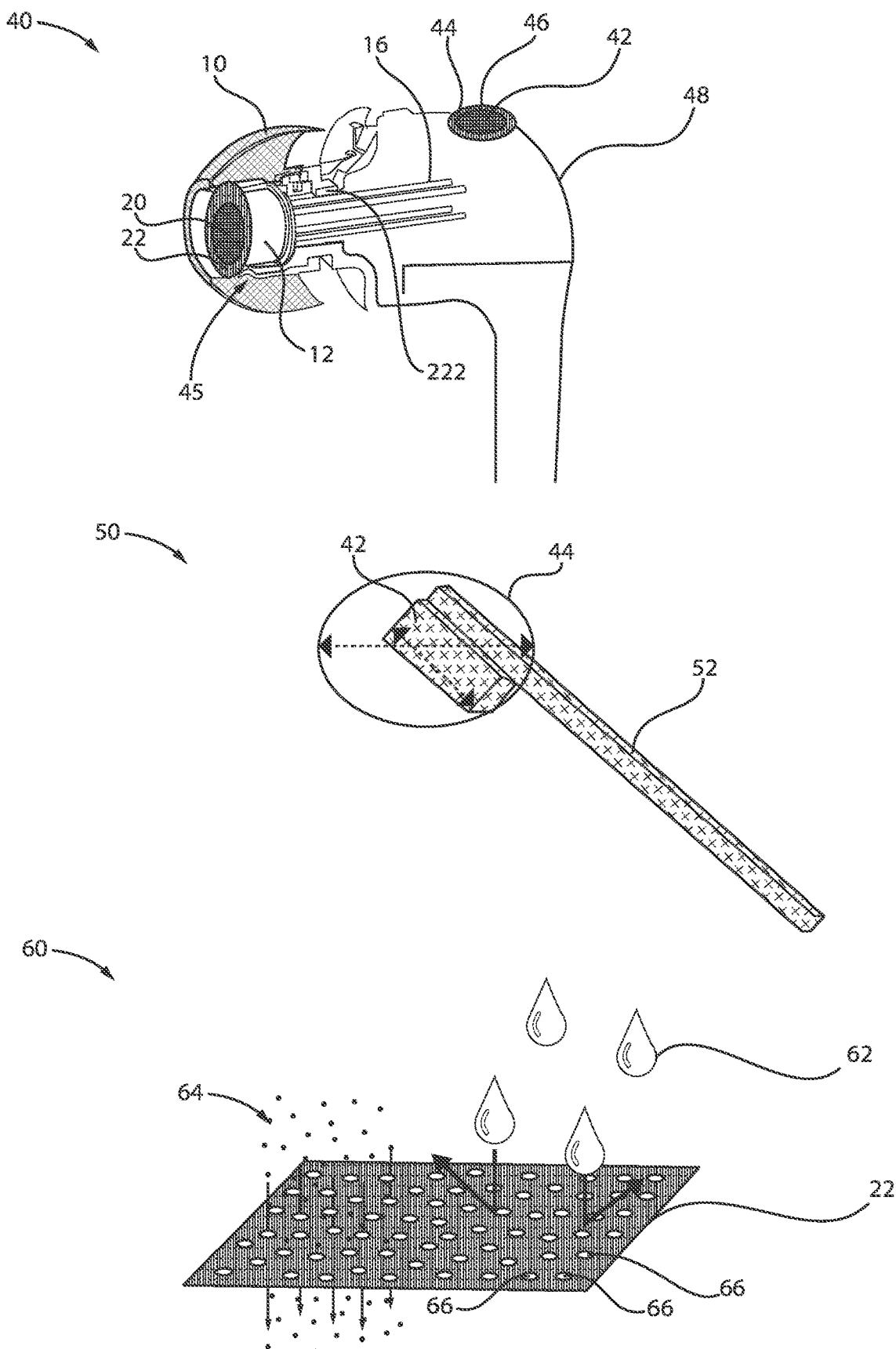
FIG. 2 illustrates a cross-sectional view on the earbud, as well as an enlarged view of the humidity sensor and the waterproof moisture (humidity) permeable membrane in action, in accordance with an embodiment of the present invention.

FIG. 2 illustrates a cross-sectional view on the earbud, as well as an enlarged view of the humidity sensor and the waterproof moisture (humidity) permeable membrane in action, in accordance with an embodiment of the present invention.

The cross-sectional view 40 illustrates the IR temperature sensor 45 located within the ear bud 10. The IR temperature sensor 45 includes the waterproof IR transmittable film 20 and the waterproof moisture (humidity) permeable membrane 22.

The ear bud 10 accommodates a first humidity sensor 222 and the headphone section 48 accommodates a second humidity sensor 42. The first humidity sensor 222 is placed on the sweat flow path, whereas the second humidity sensor 42 is located on or within the headphone section 48. An opening 44 is defined on the headphone section 48 to accommodate the second humidity sensor 42. The opening 44 is for sweat to go into the ambient. A waterproof moisture (humidity) permeable membrane 46 can be placed over the opening 44 and the second humidity sensor 42.

The enlarged view 50 illustrates the second humidity sensor 42 in the opening 44, the second humidity sensor 42 attached to the headphone section 48 via a flexible printed circuit (FPC) board component 52. The opening 44 can have a diameter of, e.g., 4 mm. The second humidity sensor 42 can have a length of, e.g., 2.5 mm.

Illustration 60 depicts the waterproof moisture (humidity) permeable membrane 22 and how water drops 62 are prevented from penetrating the waterproof moisture (humidity) permeable membrane 22. Illustration 60 further depicts moisture 64 penetrating the waterproof moisture (humidity) permeable membrane 22. The water drops 62 have a size of approximately 100-3000 µm, whereas moisture 64 has a size of approximately 0.0004 µm. The openings 66 of the waterproof moisture (humidity) permeable membrane 22 are configured to prevent water drops 62 and allow penetration by moisture 64 therethrough. Thus, by controlling the pore size 66 of the waterproof moisture (humidity) permeable membrane 22, moisture 64 can enter and water drops 62 can be prohibited from entry.

Figure 6:
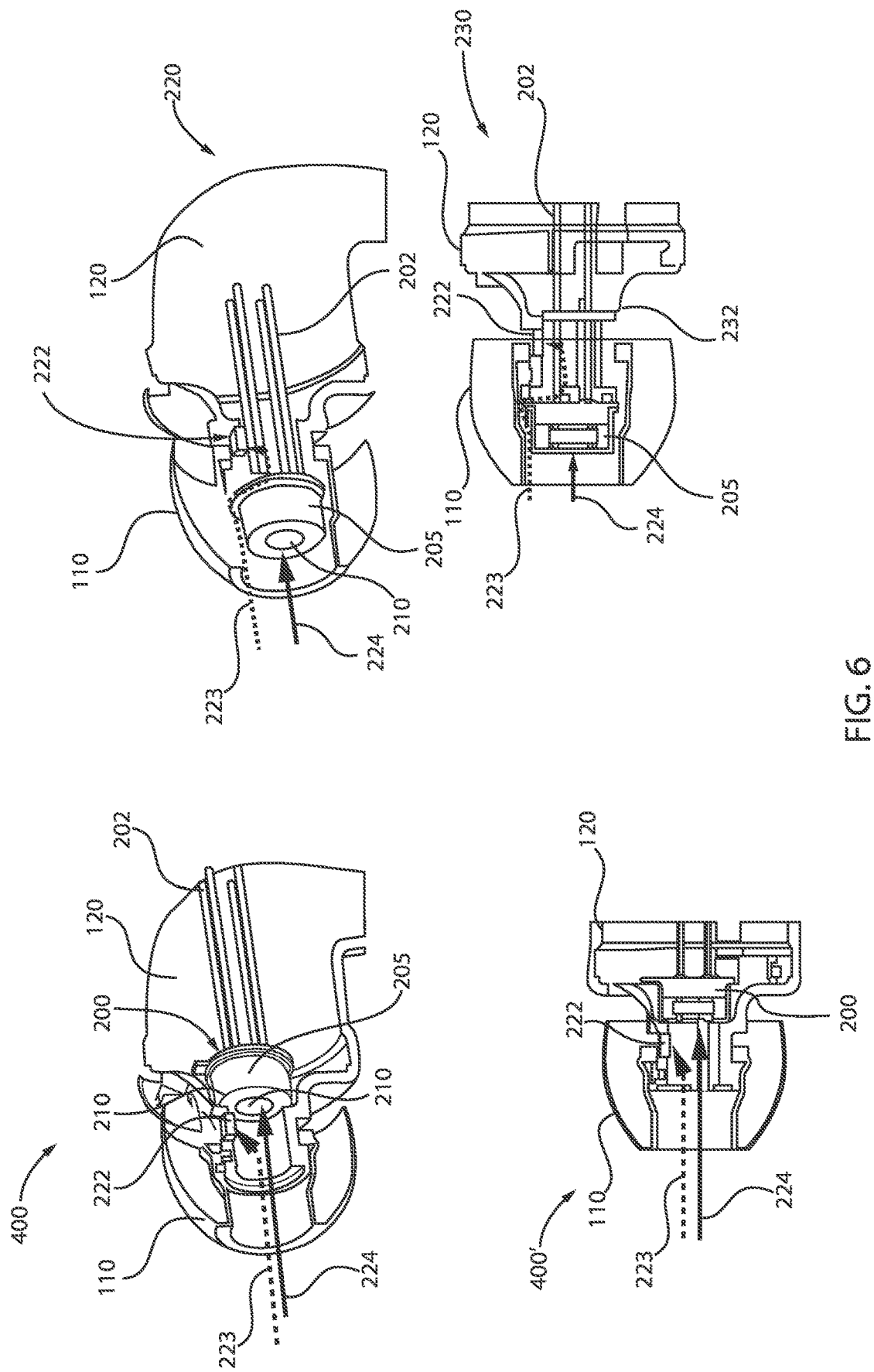
FIG. 6 illustrates cross-sectional views of the earbud of FIG. 3 depicting positioning of the sweat sensor within the earbud, in accordance with an embodiment of the present invention.

Thus, FIGS. 1 and 2 realize the co-existence of an IR temperature sensor 45 with dual humidity sensors 42, 222. As a result, both temperature measurements and sweat rate measurements can be collected and monitored continuously, and in real-time. Such ear bud 10 is a wearable device that can enable accurate prediction of heat stroke. It is noted that the first humidity sensor 222 can be placed either before the IR temperature sensor 45 or after the IR temperature sensor 45, as shown in FIG. 6. It is noted that other sensors, such as sodium ion ($Na^+$) concentration sensor 520 (FIG. 7) can be incorporated into the ear bud 10 (FIG. 1).

Figure 3:
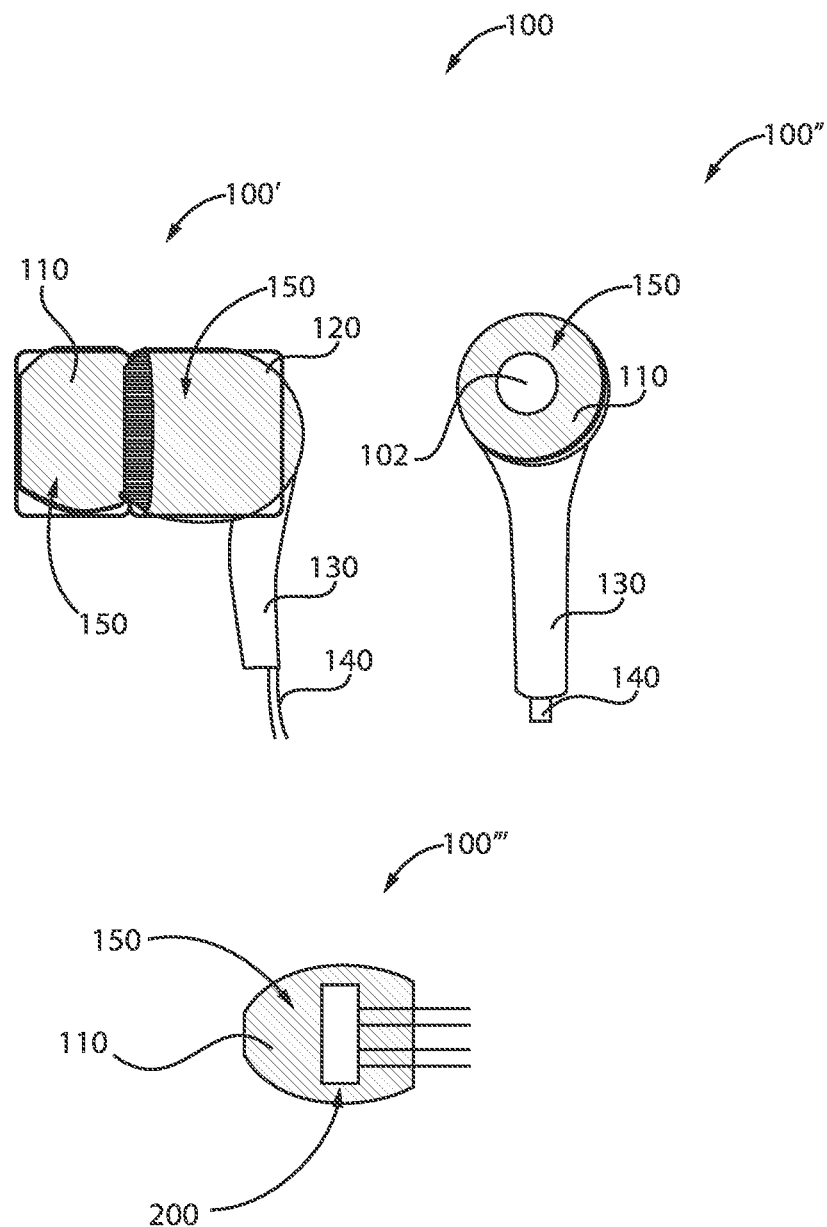
FIG. 3 illustrates several views on an earbud coated with a polymer absorbing membrane, in accordance with another embodiment of the present invention.

FIG. 3 illustrates several views on an earbud coated with a polymer absorbing membrane, in accordance with another embodiment of the present invention.

A side view 100' of the earbud 100 depicts earbud tips 110, a headphone 120, a headphone shaft 130, and an earbud wire 140. The earbud 100 is coated with a polymer absorbing membrane 150. It is contemplated that the earbud tips 110 and the headphone 120 can be coated with the polymer absorbing membrane 150.

Evaporation of absorbed sweat to air occurs in an outer surface of the earbud 100 by allowing the polymer absorbing membrane 150 to be positioned on an outer surface of the earbud 100.

A front view 100" illustrates the earbud tips 110 coated with the polymer absorbing membrane 150. An opening 102 is present where an ear of a user of earbud tips 110 receives signals or sounds.

Figure 5:
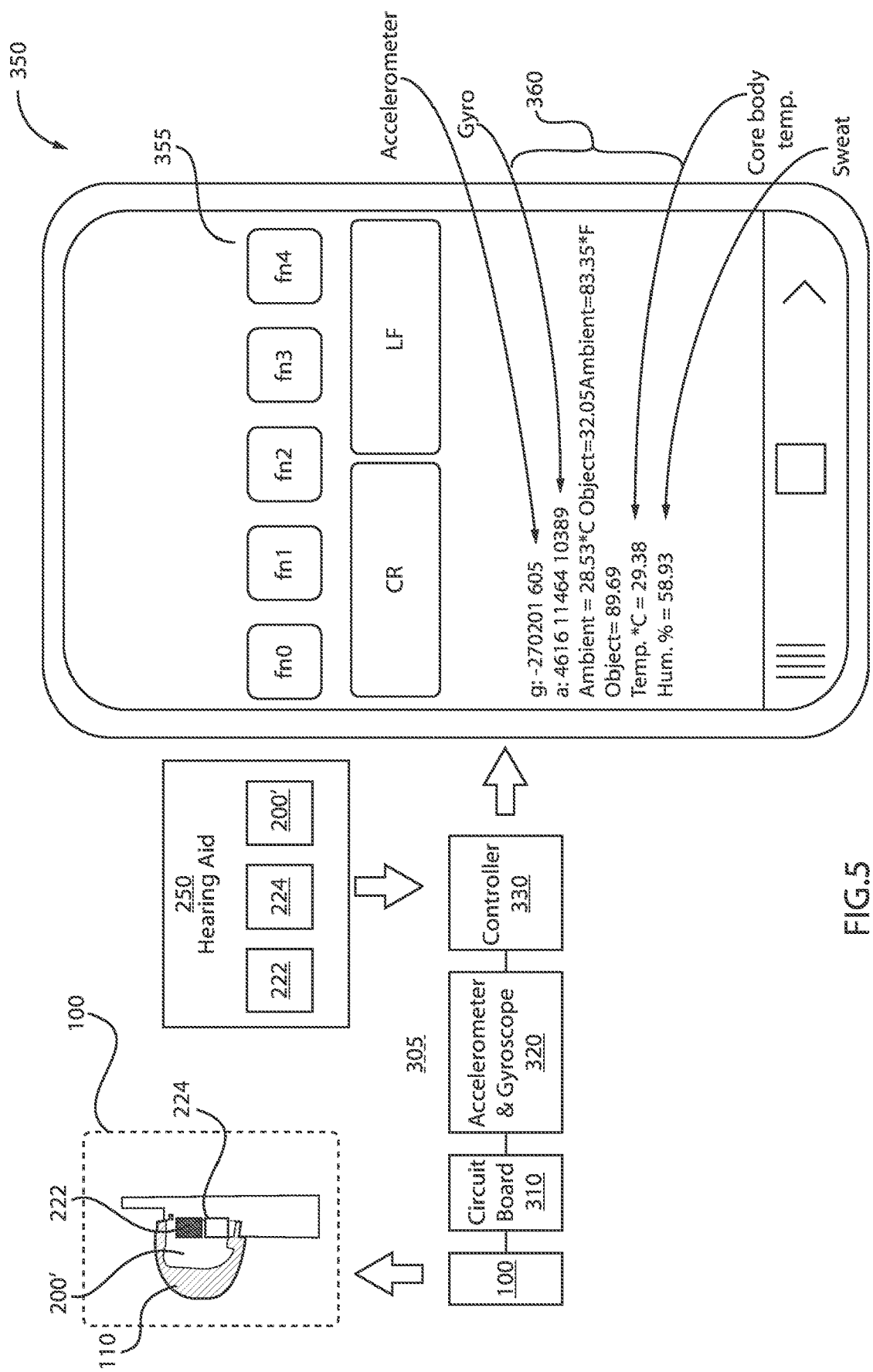
FIG. 5 illustrates the earbud of FIG. 3 incorporated into a wearable device and communicating with a wireless communication device, in accordance with an embodiment of the present invention.

The polymer absorbing membrane 150 can assume the shape of the earbud 100, as well as any type of hearing aid 250 (FIG. 5). The polymer absorbing membrane 150 can be a waterproof moisture (humidity) permeable membrane to inhibit water drops from coming through.

A cross-sectional view 100''' illustrates an infrared (IR) temperature sensor 200 located within the earbud 100. The IR temperature sensor 200 can be located within the earbud tips 110. The IR temperature sensor 200 absorbs IR in the range of, e.g., 5.5 mm-14 mm. The IR temperature sensor 200 measures an ear drum temperature.

Figure 4:
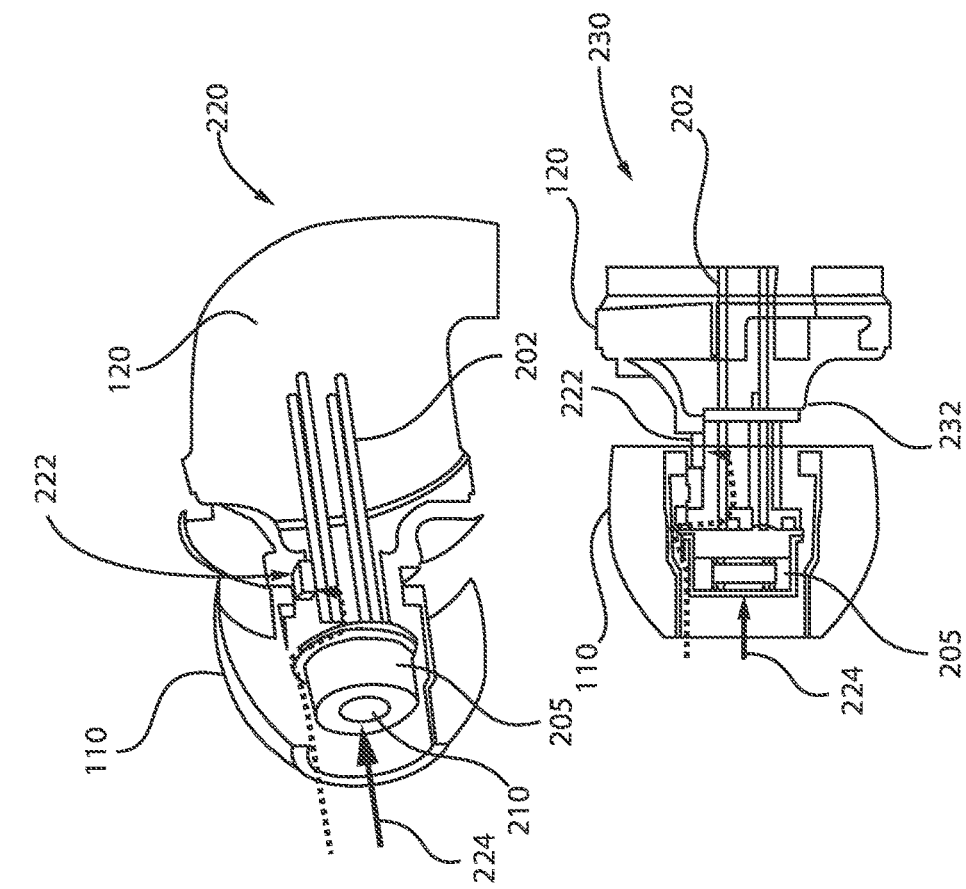
FIG. 4 illustrates cross-sectional views of the earbud of FIG. 3, where the earbud is not coated and coated with the polymer absorbing membrane, in accordance with an embodiment of the present invention.
Figure 4:
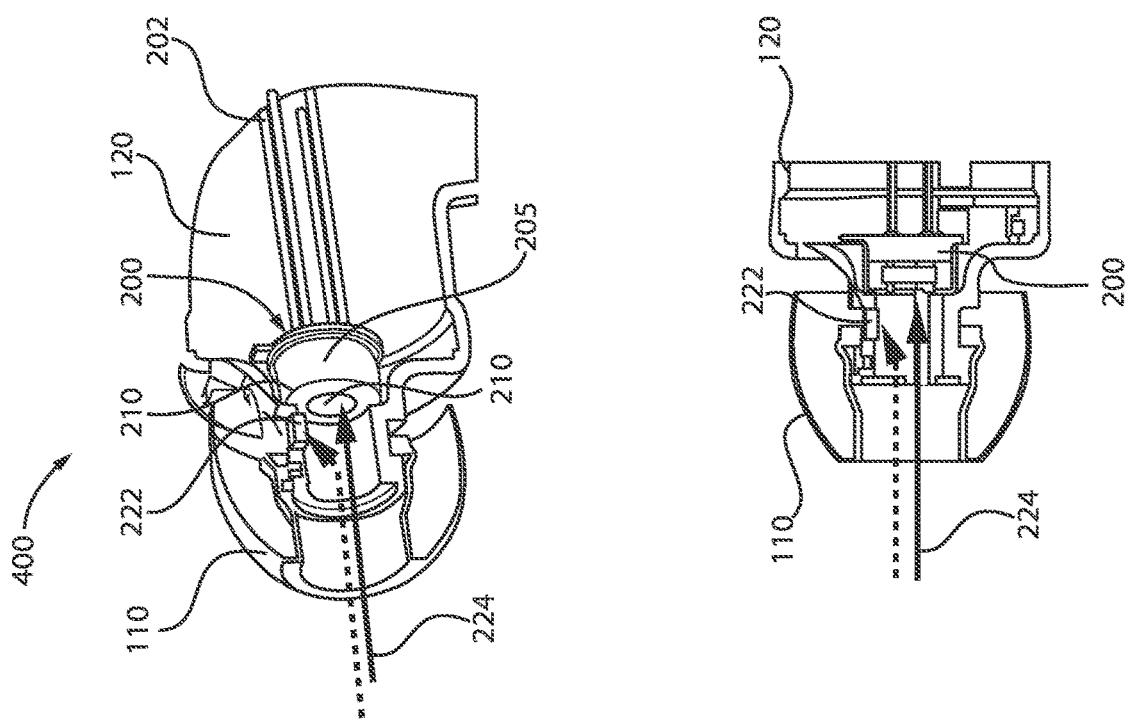

FIG. 4 illustrates cross-sectional views of the earbud of FIG. 3, where the earbud is not coated and coated with the polymer absorbing membrane, in accordance with an embodiment of the present invention.

A perspective view of the IR temperature sensor 200 is depicted. The IR temperature sensor 200 includes a metal can 205, a detector 210, and pins 202. The IR temperature sensor 200 does not include the polymer absorbing membrane 150.

Cross-sectional views 220, 230, on the left-hand side, illustrate the IR temperature sensor 200, without the polymer absorbing membrane 150, incorporated within the earbud tip 110 of the earbud 100. The metal can 205 of the IR temperature sensor 200 is located within the earbud tip 110, whereas the pins 202 of the IR temperature sensor 200 extend into the headphone 120. A sweat sensor 222 can further be located within the earbud 100. Arrow 224 illustrates the IR temperature sensor measurements. Arrow 223 illustrates the sweat rate measurements. The sweat sensor 222 or humidity sensor can be placed on a sweat flow path in the earbud 100.

The cross-sectional view 230 further illustrates an inner air close-off area 232.

The cross-sectional views 220, 230 illustrate the conventional configuration of an earbud.

In contrast, cross-sectional views 220', 230', on the right-hand side, illustrate the earbud 100 with the polymer absorbing membrane 150. The IR temperature sensor 200' includes or is coated with the polymer absorbing membrane 150. Once again, a sweat sensor 222 can further be located within the earbud 100. Arrow 224 illustrates the direction of signals or sounds entering the IR temperature sensor 200'.

The cross-sectional views 220', 230' illustrate the IR temperature sensor 200' coated in its entirety with the polymer absorbing membrane 150.

The cross-sectional view 230' further illustrates an inner air close-off area 232.

FIG. 5 illustrates the earbud of FIG. 3 incorporated into a wearable device and communicating with a wireless communication device, in accordance with an embodiment of the present invention.

In one exemplary embodiment, the earbud 100 communicates with engine 305 including a circuit board 310, an accelerometer and gyroscope 320, and a controller 330. The engine 305 can communicate with an electronic device, such as a wireless electronic device 350. The wireless electronic device 350 can be a smart phone or tablet or other computing device. The earbud 100 can include the sweat sensor 222 and a sodium ion ($Na^+$) concentration sensor 224. The sensors 222, 224 can be located anywhere within the earbud 100. In one example the sensors 222, 224 are included or embedded or incorporated in the earbud tips 110. Additionally, the IR temperature sensor 200' is located or positioned within the earbud tips 110 along with the sensors 222, 224.

The sensors 200', 222, 224 can communicate directly with each other and/or relay telemetry data directly to base receiving RF device(s) or base receivers. The base receivers can forward the telemetry data to a base computer either through a direct link or through a Network System. Alternatively, the telemetry data can be forwarded to end user devices, including but not limited to, laptops, mobile devices and the like, either directly or through a Network System. A comprehensive telemetry system using RF technologies such as UWB, ZigBee, Wi-Fi, GPS data system can be utilized to transmit the sensor data collected by sensors 200', 222, 224. The sensor data can collectively provide information related to heat stroke conditions.

The wireless electronic device 350 can display functions 355, as well as information 360. The information 360 can be, e.g., information or data obtained continuously and in real-time, and related to at least, e.g., accelerometer data, gyroscope data, core body temperature data, sweat data, $Na^+$ concentration data, etc.

In another exemplary embodiment, the hearing aid 250 communicates with engine 305 including a circuit board 310, an accelerometer and gyroscope 320, and a controller 330. The engine 305 can communicate with an electronic device, such as a wireless electronic device 350. The wireless electronic device 350 can be a smart phone or tablet or other computing device. The hearing aid 250 can include the sweat sensor 222 and the sodium ion ($Na^+$) concentration sensor 224. The sensors 222, 224 can be located anywhere within the hearing aid 250 in cooperation with the IR temperature sensor 200' coated with the polymer absorbing membrane 150.

The controller 330 can include a wired or wireless communications module (e.g., transmitter or receiver or transceiver) and can be included as needed for performing one or more of the functions of the smart wearable device described herein. Examples of wireless communication capabilities that can be provided include, but are not limited to, Bluetooth, Wi-Fi, infrared, cellular, and near field communication. One or more conventional interfaces or controllers 330 can also be provided if needed. Examples of interfaces or controllers include, but are not limited to, analog to digital converters, digital to analog converters, buffers, etc.

The controller 330 can include one or more processors. The wearable device 100, 250 can also communicate data processed at the processor to another device over a communication network (e.g., LAN such as Bluetooth, WiFi and/or WAN such as internet or a cellular network). For example, the processor can communicate with other outside devices such as a cell phone 350 over a communications link and can send and receive control commands with the outside device including commands based on the classification of sensor data from the wearable device 100, 250. The programming at the processor can also control the sensors 200', 222, 224, of the wearable sensor device in the event of the occurrence of certain environmental classifications. Some sensors can be activated or turned off for a period of time depending on the current environment and sensor data classifications.

The programming at processor can also provide a notice or alarm function using one or more haptic devices and non-haptic devices that can notify the wearer of the wearable sensor device 100, 250 of the occurrence of a variety of events. For example, the alarm can actuate when the classifications cause a change in a function of the wearable device 100, 250. A notification in the form of a vibration at a particular frequency could also occur when a communication with an outside device occurs, when the wearable device 100, 250 has automatically updated its software or when the external temperature of the environment exceeds a selected high or low. In the exemplary embodiments of the present invention, an alarm or notification can be communicated to the user when heat stroke factors exceed one or more thresholds. Thus, various heat stroke data can be communicated directly to the user or wearer of the device 100, 250 continuously and in real-time. Notifications to the user can include, messages prompting the user to drink more water.

Accordingly, the controller 330 enables a wearable device 100, 250 to automatically generate appropriate responses by a wearable sensor device and associated non-wearable devices that account for the biological status (e.g., heat stroke indication) of the wearer or current environment of the wearable device 100, 250 without any intervention by the wearer.

Depending on the function(s) described herein, the engine 305 can also include a feedback loop for machine learning or other adaptive functions. The feedback loop can also provide for device calibration based on the heat stroke feedback data.

In an example embodiment, the processor associated with the controller 330 can be further operable to detect current user location, e.g., using a global positing system (GPS) unit. The processor can be operable to detect presence of premises associated with the user in proximity to the current user location.

In a further example embodiment, the processor of the wearable device 100, 250 can be operable to detect presence of another wearable device 100, 250 in proximity to the first device. Based on the detecting, the processor can be operable to initiate data transmission between the first device, e.g., 100 and the second device, e.g., 250. Thus, the user of the first device 100 can track and be informed of whether the user of the second device 250 is experiencing heat stroke symptoms. For example, an elderly couple can both wear a hearing aid 250 and check on each other for symptoms of heat stroke. In a non-limiting example, the elderly couple can be walking, e.g., in a large park and separate from each other. If one spouse remains in the sun and is predicted to experience heat stroke (based on his hearing aid), the other spouse can be notified, by, e.g., wireless device 350 that her significant other is in danger, and in need of help. Therefore, communication can also be enabled between two or more wearable devices 100, 250.

Moreover, as a non-limiting example, the accelerometer of 320 detects acceleration, and, thus, user activity. The accelerometer provides a voltage output that is proportional to the detected acceleration. Accordingly, the accelerometer senses vibration. This voltage output provides an acceleration spectrum over time and information about time can be ascertained by performing calculations on that spectrum.

FIG. 6 illustrates cross-sectional views of the earbud of FIG. 3 depicting positioning of the sweat sensor within the earbud, in accordance with an embodiment of the present invention.

The cross-sectional views 220, 230 on the right-hand side illustrate the sweat sensor 222 positioned behind the metal can 205 of the IR temperature sensor 200' including the polymer absorbing membrane 150.

The cross-sectional views 400, 400' on the left-hand side illustrate the sweat sensor 222 positioned in front of or before the metal can 205 of the IR temperature sensor 200' including the polymer absorbing membrane 150.

Therefore, the sweat sensor can be positioned in various locations within the earbud 100 or the hearing aid 250.

It is noted that the sodium ion (Na$^+$) concentration sensor 520 (FIG. 7) can also be positioned anywhere within the earbud 100 or the hearing aid 250.

Moreover, redundant sweat affects the preciseness of core body IR temperature sensor 200. To avoid fluctuations in the temperature measured by the IR temperature sensor 200, the IR temperature sensor is coated with a polymer absorbing membrane 150, thus forming, IR temperature sensor 200', which can reduce such fluctuations. The polymer absorbing membrane 150 can absorb redundant sweat. Additionally, for the sweat measurement, a pair of humidity sensors are employed to measure the differential humidity in the ear canal and the ambient.

Figure 7:
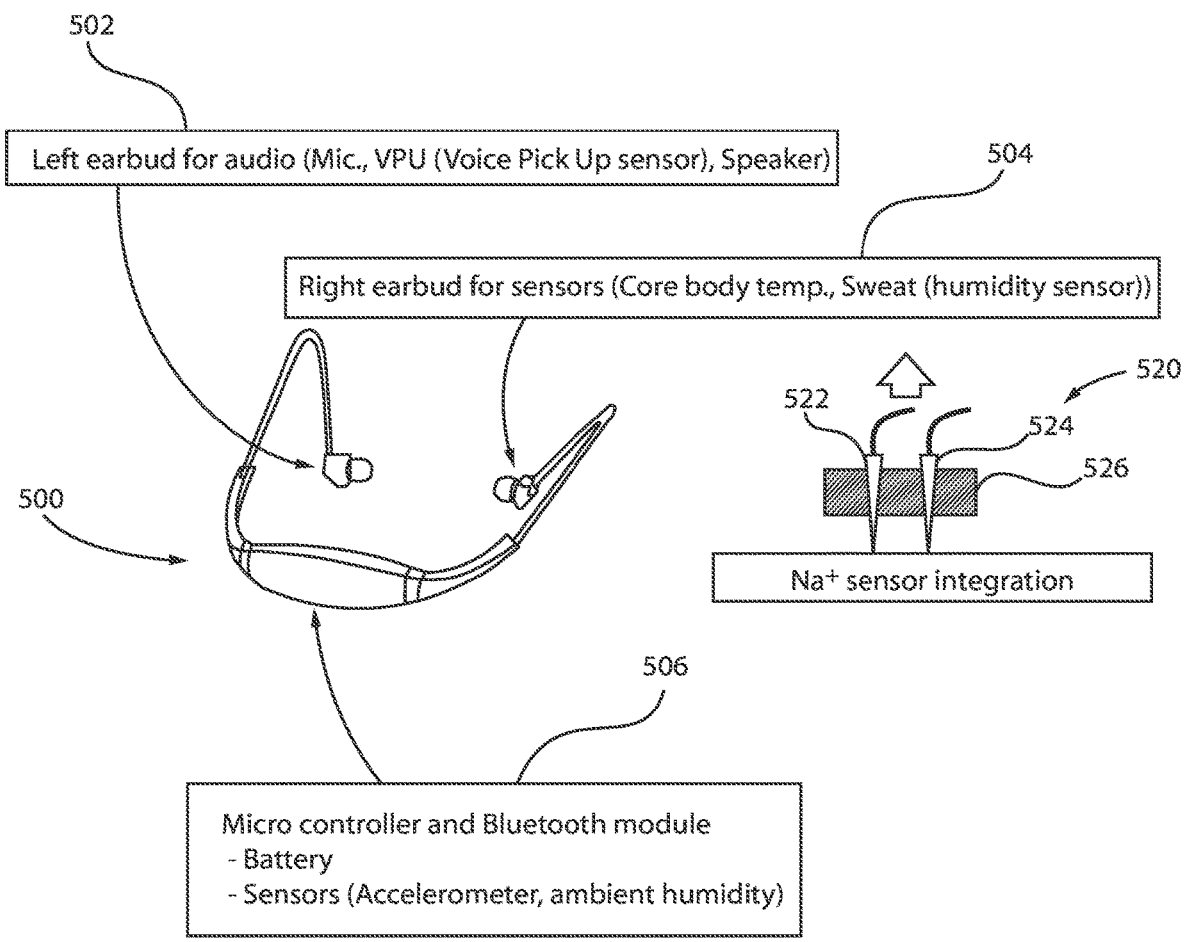
FIG. 7 is a perspective view of a wearable device including the earbuds of FIG. 3, in accordance with an embodiment of the present invention.

FIG. 7 is a perspective view of a wearable device including the earbuds of FIG. 3, in accordance with an embodiment of the present invention.

An earphone device 500 includes a first earbud 502 and a second earbud 504. The first earbud 502 can be employed for audio capabilities, and can include, e.g., a microphone, a voice pick-up (VPU) sensor, and a speaker. The second earbud 504 can incorporate sensors, such as, e.g., temperature sensors, sweat sensors, Na$^+$ concentration sensors, etc. The Na$^+$ concentration sensor 520 can include a flexible material 526, such as, e.g., a NaCl-filled flexible material. The flexible material 526 can include a first needle or first electrode 522 and a second needle or second electrode 524. The Na$^+$ concentration sensor 520 can further be used in measuring electromotive force (EMF). In one embodiment, the first electrode 522 if a Na$^+$ sensing electrode and the second electrode 524 is a silver/silver chloride (Ag/AgCl) measuring electrode. The needles 522, 524 can be configured to penetrate the epidermis to realize pain-free measurements. The epidermis is 300 µm deep from the surface of the body, where a person doesn't feel pain. How deep the needle 522, 524 penetrates is measured by the contact resistance between the needle 522, 524 and the epidermis.

Referring back to FIG. 7, the earphone device 500 can also include a microcontroller and Bluetooth® module 506. The microcontroller and Bluetooth® module 506 can include a battery and sensors, such as an accelerometer, a gyroscope, a humidity sensor, etc. By the difference between the two humidity sensors, the sweat can be accurately monitored.

For the measurement of sweat rate, a humidity sensor is employed. The humidity sensor can include a humidity-sensitive-layer, such as an polymer absorbing membrane. The same polymer absorbing membrane can be coated around an IR temperature sensor to absorb redundant sweat in the ear. By employing the same polymer absorbing membrane, the sweat rate measurement is not affected. Also, both the core body temperature (the ear drum temperature) and the sweat rate measurement are compatible. By making the polymer absorbing membrane come out of an ear, evaporation of absorbed sweat into air occurs and the saturation of sweat absorption is avoided.

Figure 8:
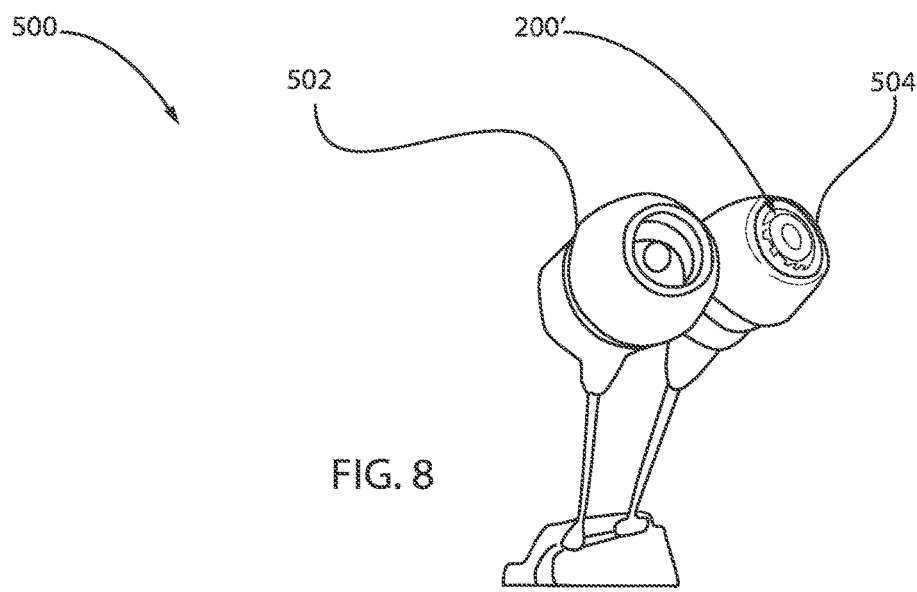
FIG. 8 is an enlarged view of the earbuds of FIG. 7, in accordance with an embodiment of the present invention.

FIG. 8 is an enlarged view of the earbuds of FIG. 7, in accordance with an embodiment of the present invention.

The enlarged view of the earphone device 500 depicts the first and second earbuds 502, 504, where the IR temperature sensor 200' with the polymer absorbing membrane 150 is depicted.

Concerning the term "wearable device," wearable technology, wearables, fashion technology, or fashion electronics are smart electronic devices (e.g., electronic device with micro-controllers) that can be incorporated into clothing or worn on the body as implants or accessories. Wearable devices such as activity trackers are an example of the Internet of Things, since "things" such as electronics, software, sensors, and connectivity are effectors that enable objects to exchange data (including data quality) through the internet with a manufacturer, operator, and/or other connected devices, without requiring human intervention. Wearable technology is often used to monitor a user's health. Given that such a device is in close contact with the user, it can easily collect data. The present invention is not limited to only earbuds and hearing aids. Instead, wearable devices can relate to smart jewelry, such as, rings, wristbands, watches, and pins, as well as fitness trackers, smart clothing, smart watches, head-mounted displays, implantables, etc.

It will further be appreciated that, as used herein, the term "smart wearable device" means a device that would be worn or otherwise associated with the body of a user and be "connected" to the user by means of at least one sensor for sensing one or more biological or physiological conditions of the user.

A used herein, the term "wearable device" is anything that can be worn by an individual and that has a back side that in some embodiments contacts a user's skin, such as an inner surface of an ear or ear drum. Examples of wearable devices include but are not limited to a cap, arm band, wristband, garment, and the like. The term "wearable device" can also be a monitoring device if it includes monitoring elements.

Figure 9:
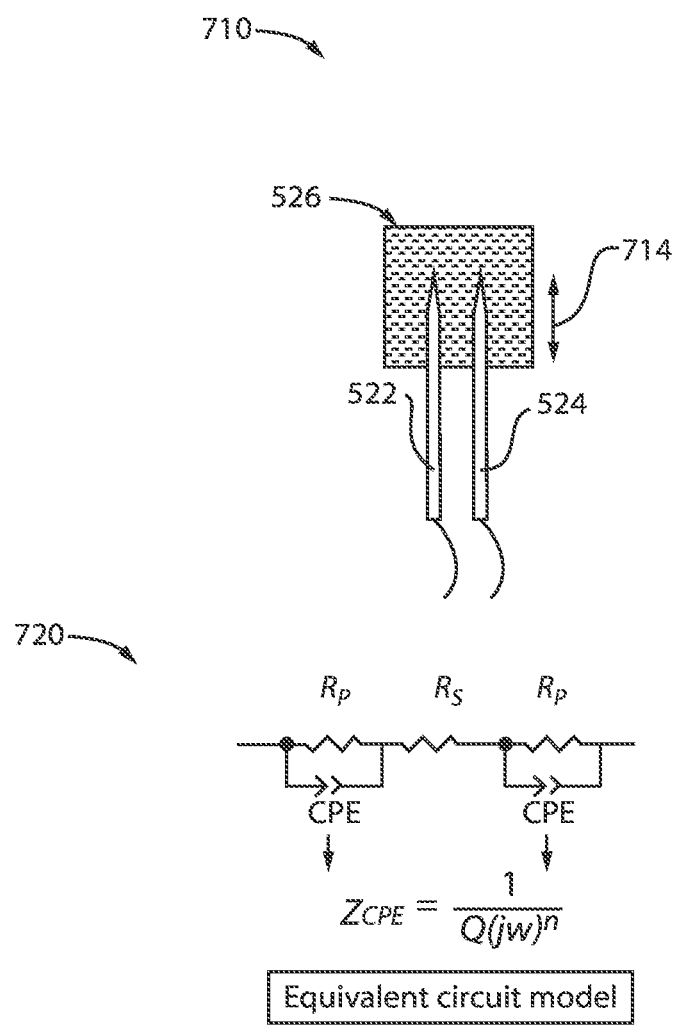
FIG. 9 illustrates contact resistance measurements between a needle and a sodium chloride (NaCl)-filled material, as well as a schematic of impedance measurement, in accordance with an embodiment of the present invention.

FIG. 9 illustrates contact resistance measurements between a needle and a sodium chloride (NaCl)-filled material, as well as a schematic of impedance measurement, in accordance with an embodiment of the present invention.

The $Na^+$ concentration sensor 520, 710 can include a flexible material 526, such as, e.g., a NaCl-filled flexible material. The flexible material 526 can include a first needle or first electrode 522 and a second needle or second electrode 524. The first and second electrodes 522, 524 can penetrate the flexible material 526 by a distance designated as 714.

The schematic of impedance measurement 720 is also shown.

Parameter Rs represents a resistance of the NaCl-filled flexible material 526.

Parameter Rp represents a contact resistance between the needle 522, 524 and the NaCl-filled flexible material 526.

Parameter $Z_{CPE}$ represents an impedance of a non-ideal double-layer capacitor, modeled by a Q-element between the needle 522, 524, and the NaCl-filled flexible material 526. Basically, the Q-element is a general element used to model an imperfect capacitor influenced by roughness, inhomogeneity or relaxation phenomenon of the electrode surface.

Q represents an admittance of an ideal capacitance.

"n" represents an empirical constant (when 0: pure resistor; when 1: pure capacitor).

"w" represents the frequency.

The contact resistance between a needle 522, 524 and the NaCl-filled flexible material 526 is expected to be dependent on how deep the needles 522, 524 penetrate the NaCl-filled flexible material 526. The contact resistance is dependent on the penetration depth. For example, when the penetration depth increases by 1 mm, the contact resistance decreases by 1270Ω. By measuring the contact resistance, a user can keep the penetration depth constant.

Figure 10:
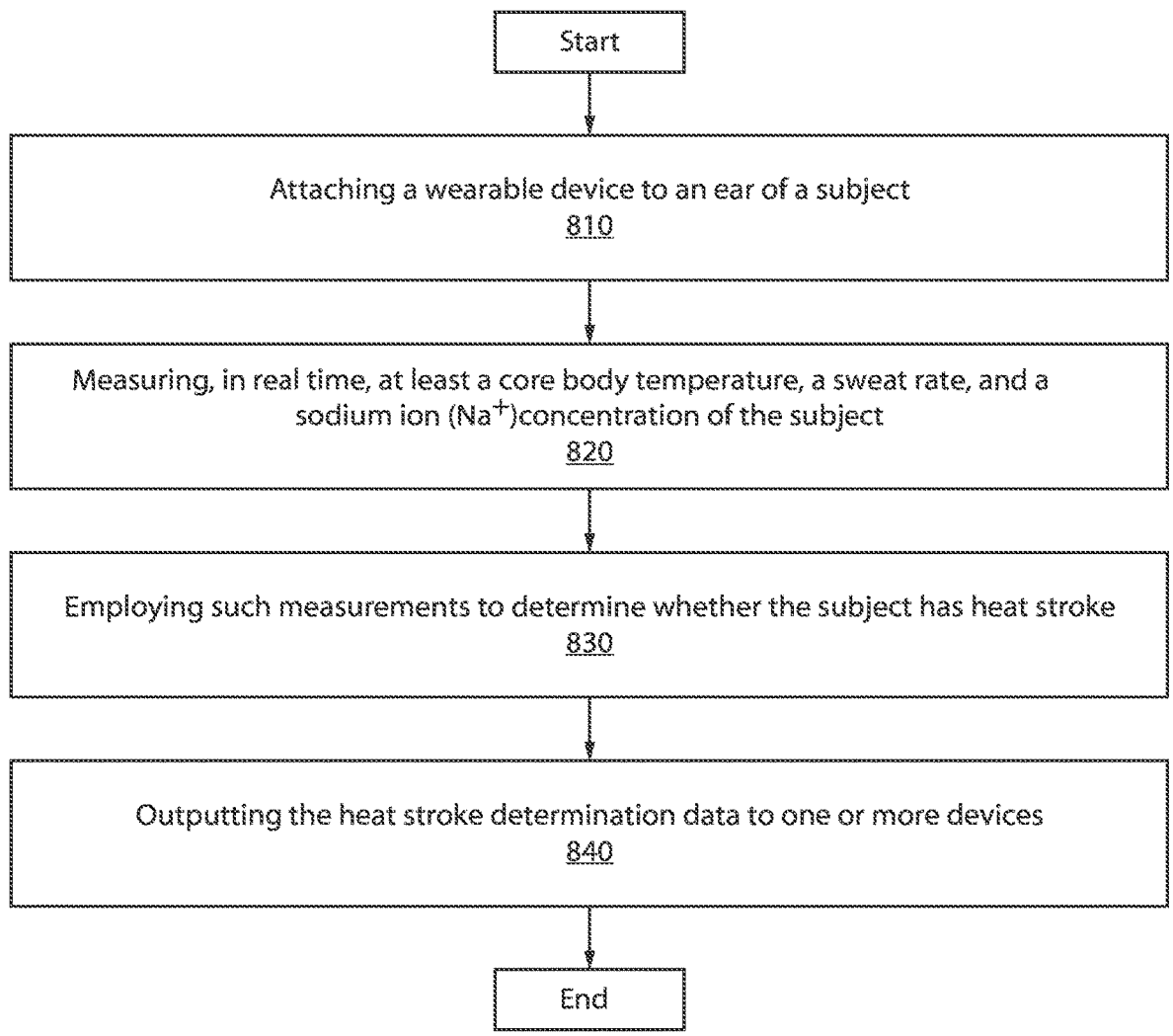
FIG. 10 is a block/flow diagram of a method for determining heat stroke of a subject, in accordance with an embodiment of the present invention.

FIG. 10 is a block/flow diagram of a method for determining heat stroke of a subject, in accordance with an embodiment of the present invention.

At block 810, a wearable device is attached to an ear of a subject.

At block 820, at least a core body temperature, a sweat rate, and a sodium ion ($Na^+$) concentration of the subject are measured in real-time.

At block 830, such measurements are employed to determine whether the subject has heat stroke.

At block 840, the heat stroke determination data is output to one or more devices.

Figure 11:
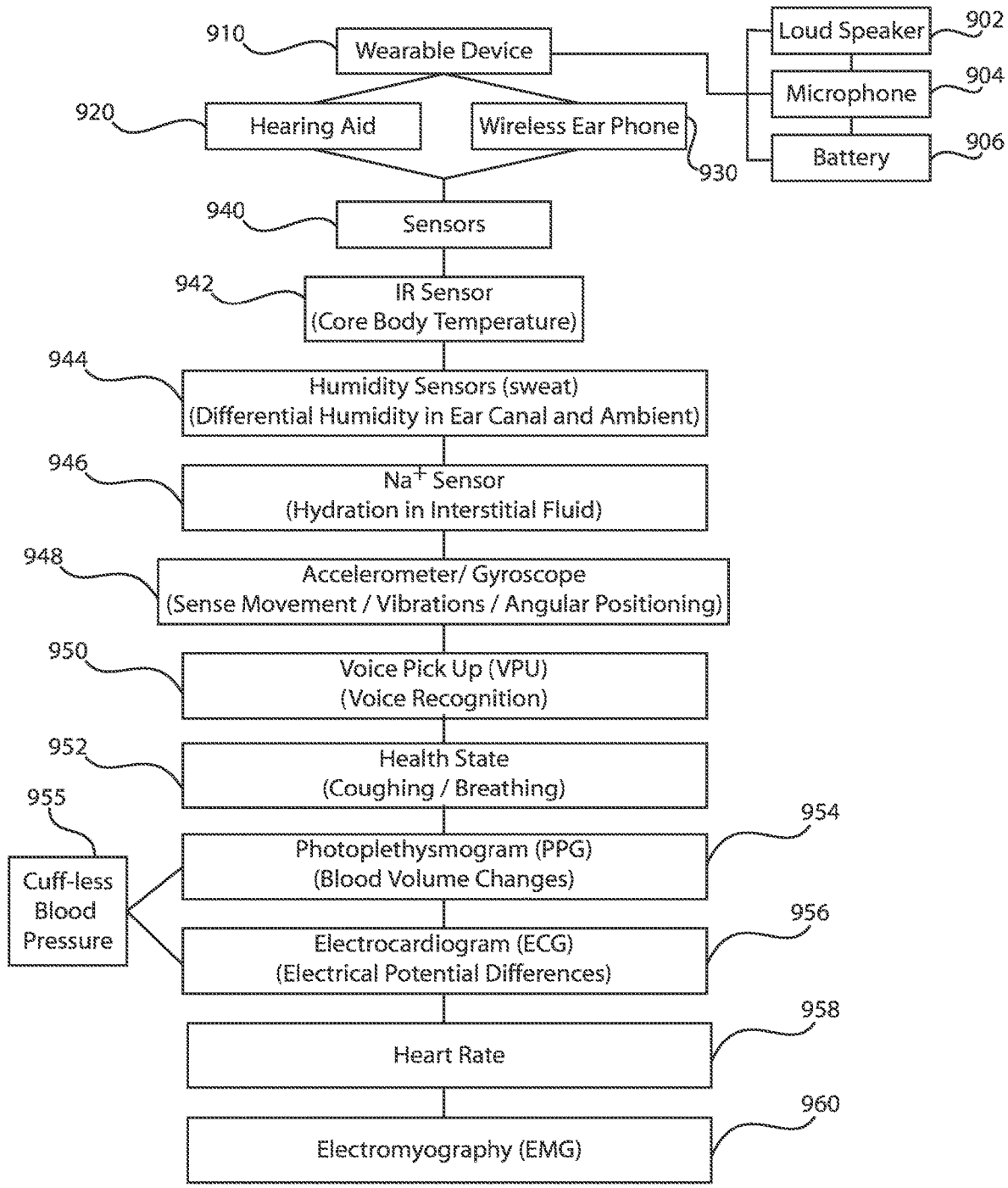
FIG. 11 is a block/flow diagram of sensors that can be incorporated in the wearable device that detects heat stroke, in accordance with an embodiment of the present invention.

FIG. 11 is a block/flow diagram of sensors that can be incorporated in the wearable device that detects heat stroke, in accordance with an embodiment of the present invention.

The wearable device 910 (or 100, 250) can include a loud speaker 902, a microphone 904, and a battery 906. The wearable device 910 can be, in one instance, a hearing aid 920. The wearable device 910 can be, in another instance, a wireless ear phone 930. The wearable devices 920, 930 can include a plurality of sensors 940.

The sensors 940 can be an infrared (IR) sensor 942 for sensing core body temperature, a humidity sensor or sweat sensor 944 for sensing differential humidity in the ear canal an in the ambient, a sodium concentration ($Na^+$) sensor 946 for sensing hydration in interstitial fluid, an accelerometer and gyroscope 948 for sensing movement, vibrations, and angular positioning, a voice pick-up (VPU) sensor 950 including voice recognition capabilities, a health state sensor 952 for detecting, e.g., coughing or breathing, a photoplethysmogram (PPG) sensor 954 for sensing blood volume changes, an electrocardiogram (ECG) sensor 956 for sensing electrical potential differences, a heart rate sensor 958 for sensing heart rates, and a electromyography (EMG) sensor 960. The PPG 954 and the ECG 956 can be employed for measuring cuff-less blood pressure 955.

In conclusion, a method and system is introduced for providing an ear wearable device for early detection of a heat-stroke. More specifically, the methods and systems provide an IR temperature sensor in an earbud type wearable device to measure core temperature, the IR temperature sensor further including a waterproof/hydrophobic film at the front side, providing a humidity sensor in a sweat flow path to measure differential humidity/sweat rate via a hydrophobic hole to enable the sweat to reach an ambient place and a polymer absorbing membrane covering the earbud to absorb the sweat and enable evaporation of sweat, and providing a Na$^+$ sensor to measure hydration in interstitial fluid.

Additionally, the present methods and systems provide methods and devices for covering an IR temperature sensor with an IR transmittable film (waterproof) with hydrophobic surface treatment. This film inhibits a water drop in order to cover the surface of the IR temperature sensor. The IR temperature sensor is located at a front side of an earbud type wearable device. The front side of the IR temperature sensor is almost the same as that of an ear cap. Also the IR temperature sensor does not occupy the whole front side of the ear cap for sweat to come in. Further, the front side of earbud type wearable device is covered with a waterproof moisture (humidity) permeable membrane. This film inhibits a water drop to enter, but moisture can go through, and, thus, doesn't affect the humidity sensor (sweat rate measurement). An opening is made at the upper side of the ear cap for sweat to go to ambient. One humidity sensor is placed on the sweat flow path to ambient and the opening is also covered with a waterproof moisture (humidity) permeable membrane. The other humidity sensor is placed on the sweat flow path in an earbud.

The present invention generally pertains to wearable devices that are capable of, for example, performing an action based on one or more biological or physiological characteristics of the user wearing the device. Using one or more sensors, a processor, and code executable on the processor, a wearable device can be configured to sense and process characteristics that include, but are not limited to, a wearer's physical characteristics such as gender, weight, height, body temperature, skin temperature, heart rate, respiration, blood sugar level, blood glucose level, stress/fatigue, galvanic skin response, ingestion (protein), digestion rate, metabolic rate, blood chemistry, sweat, core and skin temperature, vital signs, eye dryness, tooth decay, gum disease, energy storage, calorie burn rate, mental alertness, cardiac rhythm, sleep patterns, caffeine content, vitamin content, hydration, blood oxygen saturation, blood cortisol level, blood pressure, cholesterol, lactic acid level, body fat, protein level, hormone level, muscle mass, pH, etc. Such conditions can also include, but are not limited to, position (e.g., prone, upright), movement, or physical state (e.g., sleeping, exercising), etc.

A wearable device can include one or more output devices that include, but are not limited to, haptic output devices, telemetry devices, visual devices, audible devices, and other output devices.

A wearable device can include artificial intelligence so that the device can learn and adapt to the wearer. The device can be configured to accurately discriminate between erroneous (accidental, unintended, etc.) and valid sensory inputs, thereby developing accurate conclusions about a wearer's physical state or characteristics (e.g., the device does not interpret a wearer rolling over in their sleep as the wearer exercising). The device can also include one or more cameras or other visual sensors for facial, user, or other image recognition. A wearable device can also be configured to transmit information to and/or retrieve information from a wearer's digital health history, including past heat stroke incidents.

A wearable device can be configured to output information to a user, to another wearable device, to a non-wearable device, or to a network according to the particular features and function of the device.

An embodiment of a wearable device according to the present invention can have at least one sensor that acquires contextual data from the environment surrounding the wearer of the wearable device. The device can store the acquired data in memory for processing with a processor within the device or the data can be transmitted through an optional communications link to a remote computer for processing or to cloud storage. The wearable apparatus also has a number of output devices and control capabilities.

In various embodiments, the wearable device 100, 250, 920, 930 can be made as a whole piece or segment, or in separate segments that can be coupled together, (i) mechanically, (ii) by adhesion, (iii) by heat staking, (iv) with magnets, (v) other coupling mechanisms, and the like.

In another embodiment, Artificial Intelligence (AI) or Machine Learning-grade algorithms can be used to identify the user's activities, behaviors, behaviors, and perform analysis. Examples of AI algorithms include Classifiers, Expert systems, case based reasoning, Bayesian Network Systems, and Behavior based AI, Neural networks, Fuzzy systems, Evolutionary computation, and hybrid intelligent systems. The machine-learning algorithms can be heat stroke related machine-learning algorithms that are continuously updated, in real-time, as data is collected by at least sensors 200', 222, 224. The machine-learning algorithms can enable stroke alarm signal settings to be "learned" over time. The machine-learning algorithms can provide heat stroke feedback enable the sensors to more timely and accurately predict heat stroke conditions.

It is to be understood that the present invention will be described in terms of a given illustrative architecture; however, other architectures, structures, substrate materials and process features and steps can be varied within the scope of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which usually include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of a method for predicting heat stroke of a subject (which are intended to be illustrative and not limiting), it is noted that modifications and variations can be made by persons skilled in the art in light of the above teachings. It is therefore to be understood that changes may be made in the particular embodiments described which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A wearable device comprising:
a heat stroke prediction earbud covered with a waterproof moisture permeable membrane to allow moisture penetration, the heat stroke prediction earbud including:
an infrared (IR) temperature sensor for measuring core body temperature of a subject, wherein the IR temperature sensor is covered with a waterproof IR transmittable film to inhibit water drops from contacting a detector of the IR temperature sensor;
a first humidity sensor positioned within a sweat flow path within the earbud and configured to measure humidity of the subject via sweat of the subject in the sweat flow path;
a second humidity sensor positioned on a headphone section of the earbud, and configured to measure humidity of the subject via the sweat of the subject going to ambient; and
a sodium ion ($Na^+$) concentration sensor positioned within the earbud, and configured to measure hydration levels of the subject via sodium ion concentration and interstitial fluids found in the sweat of the subject within the sweat flow path,
wherein the wearable device predicts heat stroke of the subject in real-time when the measured humidity from the first and second humidity sensors and the measured hydration levels exceed respective threshold values.

2. The wearable device of claim 1, wherein a gap is formed between the earbud and an outer rim of the IR temperature sensor.

3. The wearable device of claim 2, wherein the gap defines the sweat flow path within the earbud.

4. The wearable device of claim 1, wherein another sweat flow path to ambient is defined by an opening formed on an earphone.

5. The wearable device of claim 4, wherein the opening is covered by another waterproof moisture permeable membrane.

6. The wearable device of claim 1, wherein the first and second humidity sensors measure differential humidity between an ear canal of the subject and ambient.

7. The wearable device of claim 1, wherein the waterproof IR transmittable film is attached directly to an outer rim of the IR temperature sensor.

8. The wearable device of claim 1, wherein the waterproof moisture permeable membrane is directly attached to both an outer rim of the IR temperature sensor and a front surface of the earbud.

9. A wearable device comprising:
a pair of heat stroke prediction earbuds coated with a polymer absorbing membrane, wherein the pair of heat stroke prediction earbuds further include:
an infrared (IR) temperature sensor for measuring core body temperature of a subject;
a pair of humidity sensors for measuring differential humidity between an ear canal of the subject and ambient, one of the humidity sensors is configured to measure humidity of the subject via sweat of the subject in the sweat flow path and the other humidity sensor is configured to measure humidity of the subject via the sweat of the subject going to ambient; and
a sodium ion (Na$^+$) concentration sensor positioned within the earbud, and configured to measure hydration levels of the subject via sodium ion concentration and interstitial fluids found in the sweat of the subject within the sweat flow path,
wherein the wearable device predicts heat stroke of the subject in real-time when the measured humidity from the pair of humidity sensors and the measured hydration levels exceed respective threshold values.

10. The wearable device of claim 9, wherein earbud tips and portions of the headphone section of the pair of earbuds are coated with the polymer absorbing membrane.

11. The wearable device of claim 9, wherein the polymer absorbing membrane is coated on a metal can portion of the IR temperature sensor.

12. The wearable device of claim 9, wherein the wearable device further includes an accelerometer and a gyroscope to predict movements of the subject.

13. The wearable device of claim 9, wherein one earbud of the pair of earbuds includes at least a microphone and a voice pick-up (VPU) device.

14. The wearable device of claim 13, wherein sound analysis is performed on the microphone and the VPU device to analyze coughing and breathing states of the subject.

15. The wearable device of claim 13, wherein another earbud of the pair of earbuds includes a photoplethysmogram (PPG) sensor to determine pulse waves, a heart rate sensor to assess stress levels, and an electrocardiogram (ECG) sensor to measure electrical potential differences between ears of the subject.

16. The wearable device of claim 15, wherein measurements from the PPG sensor and the ECG sensor are combined to determine cuff-less blood pressure.

17. The wearable device of claim 9, wherein an electromyography (EMG) sensor is employed to detect non-vocal commands, including teeth clocks, tongue snaps, and jaw bone movements.

18. A method comprising:
covering a heat stroke prediction earbud with a waterproof moisture permeable membrane to allow moisture penetration;
measuring, by an infrared (IR) temperature sensor, core body temperature of a subject, wherein the IR temperature sensor is covered with a waterproof IR transmittable film to inhibit water drops from contacting a detector of the IR temperature sensor;
positioning a first humidity sensor within a sweat flow path within the earbud, the first humidity sensor configured to measure humidity of the subject via sweat of the subject in the sweat flow path;
placing a second humidity sensor on a headphone section of the earbud, the second humidity sensor configured to measure humidity of the subject via the sweat of the subject going to ambient; and
measuring, by a sodium ion (Na$^+$) concentration sensor positioned within the earbud, hydration levels of the subject via sodium ion concentration and interstitial fluids found in the sweat of the subject within the sweat flow path,
wherein the wearable device predicts heat stroke of the subject in real-time when the measured humidity from the first and second humidity sensors and the measured hydration levels exceed respective threshold values.

19. The method of claim 18, wherein the first and second humidity sensors measure differential humidity between an ear canal of the subject and ambient.

* * * * *